(12) United States Patent
Haramaki et al.

(10) Patent No.: US 7,491,841 B2
(45) Date of Patent: Feb. 17, 2009

(54) PROCESS FOR PRODUCING ACRYLIC ESTER

(75) Inventors: Hidefumi Haramaki, Himeji (JP); Manabu Matsui, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 12 days.

(21) Appl. No.: 11/822,521

(22) Filed: Jul. 6, 2007

(65) Prior Publication Data

US 2008/0015384 A1   Jan. 17, 2008

(30) Foreign Application Priority Data

Jul. 11, 2006   (JP) .............................. 2006-190889

(51) Int. Cl.
*C07C 67/48* (2006.01)
(52) U.S. Cl. .................................... 560/218
(58) Field of Classification Search ........................ None
See application file for complete search history.

(56) References Cited

U.S. PATENT DOCUMENTS

| | | | | |
|---|---|---|---|---|
| 3,882,167 | A | * | 5/1975 | Lohmar et al. .............. 560/205 |
| 4,280,009 | A | | 7/1981 | Erpenbach et al. |
| 4,956,493 | A | * | 9/1990 | Ueoka et al. ................ 560/208 |
| 6,649,787 | B1 | * | 11/2003 | Nakahara et al. ............ 560/205 |
| 6,977,310 | B2 | | 12/2005 | Ackermann et al. |

FOREIGN PATENT DOCUMENTS

| | | |
|---|---|---|
| JP | 52-57116 | 5/1977 |
| JP | 58-159442 | 9/1983 |
| JP | 63-275544 | 11/1988 |
| JP | 2-279655 | 11/1990 |
| JP | 3-34956 | 2/1991 |
| JP | 3-52842 | 3/1991 |
| JP | 3-52843 | 3/1991 |
| JP | 3-151347 | 6/1991 |
| JP | 2003-171347 | 6/2003 |
| JP | 2003-226669 | 8/2003 |
| JP | 2006-503795 | 2/2006 |

OTHER PUBLICATIONS

Notice of Reasons for Rejection issued on May 28, 2008, in Japanese Patent Application No. 2006-190889, and English translation thereof.

* cited by examiner

*Primary Examiner*—Paul A Zucker
(74) *Attorney, Agent, or Firm*—Wenderoth, Lind & Ponack, LLP.

(57) ABSTRACT

A process for producing an acrylic ester using acrylic acid and an aliphatic or alicyclic alcohol having from 5 to 8 carbon atoms, as raw materials, and using a strongly acidic cation exchange resin as a catalyst. In such a process for producing an acrylic ester, a crude acrylic ester withdrawn from the bottom of a low-boiling separation column is supplied to a rectifying column, a rectified acrylic ester is taken out from the top of the rectifying column, while a high-boiling substance containing an acrylic ester, which is withdrawn from the bottom of the rectifying column, is supplied to a high-boiling separation column and/or a thin-film evaporator to separate it into an acrylic ester component and a high-boiling substance, and the separated acrylic ester component is taken out as a distillate and supplied to the low-boiling separation column for its recovery.

8 Claims, 3 Drawing Sheets

PROCESS FOR PRODUCING ACRYLIC ESTER

BACKGROUND OF THE INVENTION

1. Field of the Invention

The present invention relates to a process for producing an acrylic ester, and more particularly, to a process for producing an acrylic ester from acrylic acid and an aliphatic or alicyclic alcohol having from 5 to 8 carbon atoms using a strongly acidic cation exchange resin.

2. Description of the Related Art

Acrylic esters can be produced from acrylic acid and various alcohols, for example, as disclosed in Japanese Patent Publication No. Shou 52-57116, by an esterification reaction using a homogeneous catalyst such as sulfuric acid or phosphoric acid, or alternatively, for example, as disclosed in Japanese Patent Laid-open Publications Nos. Hei 2-279655 and Hei 3-52843, by an esterification reaction using a heterogeneous catalyst such as a strongly acidic cation exchange resin.

In the continuous production of an acrylic ester, there have heretofore been carried out operations in which acrylic acid and an alcohol are esterified in a reactor using a catalyst such as an inorganic acid, e.g., sulfuric acid or phosphoric acid, or a strongly acidic cation exchange resin, the resulting reaction liquid is supplied to a low-boiling separation column to separate it into a high-boiling substance composed mainly of a generated acrylic ester and a low-boiling component composed mainly of an unreacted alcohol, acrylic acid, and generated water, and an acrylic ester is collected from the former high-boiling substance and circulated to the reaction system.

In a process using an inorganic acid such as sulfuric acid or phosphoric acid as an esterification catalyst (e.g., see Japanese Patent Laid-open Publication No. Shou 52-57116), the use of a highly corrosive inorganic acid has no other choice to select an anti-corrosive material for apparatus, which causes problems that the apparatus becomes expensive and the waste liquid treatment to make an inorganic acid contained in the waste liquid harmless becomes highly costly.

In an esterification reaction using an ion exchange resin, there is no drawback that will be involved when an inorganic acid is used as an esterification catalyst. As for acrylic acid to be used as a raw material, acrylic acid purified to remove low-boiling impurities and high-boiling impurities is used, the production cost of acrylic acid rises due to the removal of high-boiling impurities, and therefore, the use of unpurified acrylic acid would become advantageous. However, when acrylic acid containing a high-boiling acid component is used as a raw material, unfavorable polymerization reaction and side reaction occur, facilities such as piping systems are clogged by polymers, the unit consumption of acrylic acid or an alcohol increases, and the quality of a product is deteriorated. Thus, in Japanese Patent Laid-open Publication No. 2003-171347, there is proposed a countermeasure that the concentration of impurities such as maleic acid, β-acryloxypropionic acid (i.e., a dimer of acrylic acid), furfural, and benzaldehyde is restricted to a specific concentration or lower.

Of these high-boiling impurities, in particular, high-boiling acid components such as maleic acid and β-acryloxypropionic acid can easily be removed from waste oil in the production of an ester using a low-boiling alcohol having 4 or less carbon atoms as a raw material, thereby causing no particular problem. However, in the production of an ester using an aliphatic or alicyclic alcohol having from 5 to 8 carbon atoms as a raw material, it is difficult to separate high-boiling acid components, which has remarkable influences on the loss in quality of a product and the deterioration of the unit consumption of the main raw material, and which requires uneconomical operation, thereby causing serious problems. In particular, β-acryloxypropionic acid is generated during the storage after the acrylic acid production process, and therefore, the control of temperature and the like during the storage are sometimes required, which makes it difficult to maintain the stable quality and the low unit consumption of raw materials in the production of an acrylic ester.

SUMMARY OF THE INVENTION

Under these circumstances, it is an object of the present invention to provide a process for producing an acrylic ester with excellent economic efficiency, which can eliminate the conventional problems to maintain the stable quality and the low unit consumption of raw materials, in the process for producing an acrylic ester using acrylic acid containing high-boiling acid components such as maleic acid and β-acryloxypropionic acid influencing the loss in quality and the unit consumption of raw materials, and an aliphatic or alicyclic alcohol having from 5 to 8 carbon atoms as raw materials, and using a strongly acidic cation exchange resin as a catalyst.

The present inventors have made various studies, and as a result, they have found the following facts to complete the present invention: in the production of an acrylic ester from acrylic acid and an aliphatic or alicyclic alcohol having from 5 to 8 carbon atoms using a strongly acidic cation exchange resin, the yield of a product acrylic ester can be improved without lowering the quality of a product and the amount of waste oil can be reduced to improve production efficiency by supplying the bottom liquid of a rectifying column, in which a crude acrylic ester is rectified, to a high-boiling separation column and/or a thin-film evaporator to separate it into an acrylic ester component and a high-boiling substance, and by taking out the separated acrylic ester component as a distillate and supplying it to the low-boiling separation column for its recovery; and further, an acrylic ester can be produced at the lower unit consumption of raw materials, while maintaining the stable quality of a product, by mixing all or part of the distillate from the high-boiling separation column and/or the thin-film evaporator with water to carry out the extraction treatment of high-boiling acid components. In particular, the application of the extraction treatment is also effective for reducing the burdens on the purification of raw material acrylic acid and the storage management by making it possible to expand the width of high-boiling acid component content in acrylic acid which can be used in the production of an acrylic ester from acrylic acid influenced markedly by high-boiling acid components such as maleic acid and β-acryloxypropionic acid, and an aliphatic or alicyclic alcohol having from 5 to 8 carbon atoms.

That is, the present invention provides a process for producing an acrylic ester by supplying acrylic acid and an aliphatic or alicyclic alcohol having from 5 to 8 carbon atoms to an esterification reactor to cause an esterification reaction using a strongly acidic cation exchange resin as a catalyst in the reactor, the process comprising supplying an obtained reaction product to a low-boiling separation column to distill an alcohol, acrylic acid, and water from a top of the low-boiling separation column, and separating them into a water phase and an organic phase containing the alcohol and acrylic acid, the organic phase being circulated as a circulated liquid to the reactor, supplying a crude acrylic ester, which is withdrawn from a bottom of the low-boiling separation column, to a rectifying column, taking out a rectified acrylic ester from a top of the rectifying column, and supplying a high-boiling substance containing an acrylic ester, which is withdrawn from a bottom of the rectifying column, to a high-boiling separation column and/or a thin-film evaporator to separate it into an acrylic ester component and a high-boiling substance, the separated acrylic ester component being taken out as a distillate and supplied to the low-boiling separation column for its recovery.

The process for producing an acrylic ester according to the present invention preferably further comprises, before the distillate taken out from the high-boiling separation column and/or the thin-film evaporator is supplied to the low-boiling separation column for its recovery, mixing all or part of the distillate with water to extract and remove a high-boiling acid component contained in the distillate into a water phase, and supplying an obtained organic phase to the low-boiling separation column for its recovery. For the extraction and removal of the high-boiling acid component, a process wastewater generated in a step of producing an acrylic ester can preferably be used. The process wastewater may include reaction water generated in the esterification reaction and/or steam drain exhausted when a steam ejector is used for reducing pressure in a pressure reduction step included in a step of producing an acrylic ester. The ratio of water to be used to extract and remove the high-boiling acid component, relative to the distillate taken from the high-boiling separation column and/or the thin-film evaporator, may preferably be within a range of from 0.5:1 to 2.0:1, more preferably from 0.8:1 to 1.5:1, by mass ratio.

In the process for producing an acrylic ester according to the present invention, the acrylic acid to be used as a raw material is acrylic acid containing high-boiling acid components such as maleic acid and β-acryloxypropionic acid, for example, acrylic acid containing from 10 to 5,000 ppm of maleic acid and/or from 10 to 5,000 ppm of β-acryloxypropionic acid, preferably acrylic acid containing from 10 to 500 ppm of maleic acid and/or from 10 to 3,600 ppm of β-acryloxypropionic acid.

According to the present invention, in the production of an acrylic ester using acrylic acid and an aliphatic or alicyclic alcohol having from 5 to 8 carbon atoms as raw materials and using a strongly acidic cation exchange resin as a catalyst, the yield of an acrylic ester can be improved without lowering the quality of a product by the effective separation of the acrylic ester from high-boiling acid components influencing the quality of a product and the unit consumption of raw materials. In the extraction treatment of high-boiling acid components, process wastewater generated in a step of producing an acrylic ester, including reaction generated water, can be used as extraction water, and therefore, there is no need to introduce fresh water, from the outside of the system, leading to an increase in the amount of wastewater. Further, the application of the extraction treatment of high-boiling acid components makes it possible to separate and remove, by an inexpensive method, high-boiling acid components difficult to be separated, and to use low-purity acrylic acid containing relatively great amounts of high-boiling acid components, as well as makes it easy to carry out the storage management of acrylic acid as a raw material, thereby making it possible to broaden the accepted range of raw material acrylic acid which can be used in the production of an acrylic ester from acrylic acid and an aliphatic or alicyclic alcohol having from 5 to 8 carbon atoms.

For these reasons, the present invention can provide a process for producing an acrylic ester with very excellent economic efficiency.

DETAILED DESCRIPTION OF THE INVENTION

The process for producing an acrylic ester according to the present invention (hereinafter referred to simply as "the production process of the present invention" in some cases) is a process for producing an acrylic ester by supplying acrylic acid and an aliphatic or alicyclic alcohol having from 5 to 8 carbon atoms to an esterification reactor to cause an esterification reaction using a strongly acidic cation exchange resin as a catalyst in the reactor, the process comprising supplying an obtained reaction product to a low-boiling separation column to distill an alcohol, acrylic acid, and water from the top of the low-boiling separation column, and separating them into a water phase and an organic phase containing the alcohol and acrylic acid, the organic phase being circulated as a circulated liquid to the reactor, supplying a crude acrylic ester, which is withdrawn from the bottom of the low-boiling separation column, to a rectifying column, taking out a rectified acrylic ester from the top of the rectifying column, and supplying a high-boiling substance containing an acrylic ester, which is withdrawn from the bottom of the rectifying column, to a high-boiling separation column and/or a thin-film evaporator to separate it into an acrylic ester component and a high-boiling substance, the separated acrylic ester component being taken out as a distillate and supplied to the low-boiling separation column for its recovery.

In this case, all or part of the distillate from the high-boiling separation column and/or the thin-film evaporator may preferably be mixed with water to extract and remove a high-boiling acid component contained in the distillate into a water phase, and an obtained organic phase is supplied to the low-boiling separation column for its recovery.

In the production process of the present invention, acrylic acid containing high-boiling acid components such as maleic acid and β-acryloxypropionic acid, even if it is, for example, acrylic acid containing from 10 to 5,000 ppm of maleic acid and/or from 10 to 5,000 ppm of β-acryloxypropionic acid, and even if it may preferably be acrylic acid containing from 10 to 500 ppm of maleic acid and from 10 to 3,600 ppm of β-acryloxypropionic acid as shown in Examples described below, can be used as a raw material. Incidentally, high-boiling acid components contained in acrylic acid can be analyzed by, for example, gas chromatography.

As an aliphatic or alicyclic alcohol having from 5 to 8 carbon atoms (hereinafter referred to simply as "the alcohol" in some cases), there can be mentioned, although not particularly limited thereto, so long as an acrylic ester can be formed using a strongly acidic cation exchange resin, for example, 2-ethylhexanol and cyclohexanol. Such an alcohol may be linear or branched. Further, an unreacted alcohol recovered from the low-boiling separation column after the esterification reaction is circulated and recycled.

In the production process of the present invention, a strongly acidic cation exchange resin is used as a catalyst for esterification reaction. In the case of a strongly acidic cation exchange resin, a porous or gel type resin can be used, and a porous type resin may preferably be used. In particular, when a low-purity acrylic acid is used, a porous type resin having excellent resistance to organic contamination may preferably be used. As a porous type strongly acidic cation exchange resin, for example, there may preferably be used those which have a degree of cross-linking of from 2% to 16%, a porosity of from 0.1 to 1.0 mL/g, and an average pore diameter of from 10 to 60 nm, specific examples of which are C-26C (available from Duolite International Co.), PK-208, PK-216, PK-228 (available from Mitsubishi Chemical Corporation), MSC-1, 88 (available from The Dow Chemical Company), Amberlyst-16 (available from Rohm and Haas Company), SPC-108, and SPC-112 (available from Bayer AG).

The esterification reaction is carried out by monitoring the conversion of acrylic acid through analyzing the compositions of an inlet liquid and an outlet liquid in the reactor, and adjusting the reaction temperature so that the conversion of acrylic acid becomes substantially constant. The conversion of acrylic acid may preferably be within a range of from −5% to +5%, more preferably from −3% to +3%, based on the conversion of acrylic acid in the steady state reached after the start of operation.

The esterification reaction may preferably be carried out within a range of from 50° C. to 100° C., more preferably from 70° C. to 100° C., although depending on the intended esterification reaction. Further, the esterification reaction is carried out in a liquid phase, and the type of reaction may be on a fluid or fixed bed.

In the esterification reaction, a polymerization inhibitor can be used as applied in ordinary cases. Examples of the polymerization inhibitor may include hydroquinone, methoxyhydroquinone, phenothiazine, hydroxylamine, and phenylenediamine. Incidentally, the effect of a polymerization inhibitor can further be enhanced when the esterification reaction is carried out in the presence of molecular oxygen.

The thus obtained esterification reaction product is supplied to a low-boiling column for its distillation, and substantially all the amount of high-boiling substance composed mainly of a generated acrylic ester is withdrawn from the bottom of the low-boiling separation column and supplied to a rectifying column for its distillation, thereby obtaining a product acrylic ester as a distillate from the top of the rectifying column.

On the other hand, from the top of the low-boiling separation column, low-boiling components composed mainly of an unreacted alcohol, unreacted acrylic acid, and generated water are distilled and condensed to separate them into a water phase and an organic phase composed mainly of an alcohol and acrylic acid. The organic phase is circulated as a circulated liquid to the reactor. On the other hand, the water phase may be discarded as wastewater or may be recycled as process wastewater.

To allow the esterification reaction to proceed smoothly, it is advantageous to decrease the amounts of acrylic ester and water and to increase the amounts of alcohol and acrylic acid in the composition of a circulated liquid. Therefore, as for the circulated liquid, although depending on the intended acrylic ester and reaction conditions, the total amount of alcohol and acrylic acid may preferably be 50% by mass or higher, more preferably 60% by mass or higher, and the concentration of water may preferably be 5% by mass or lower, more preferably 2% by mass or lower. Further, the amount of circulated liquid to be circulated to the reactor is not preferred when it is too high or too low because of an increase in the amount of catalyst necessary for the esterification reaction. The amount of circulated liquid may suitably be from 1 to 5 times the total amount of alcohol and acrylic acid newly supplied.

A polymerization inhibitor can also be used in the low-boiling separation column. Examples of the polymerization inhibitor may include the same as exemplified regarding the esterification reaction. In the same manner as described above, the effect of a polymerization inhibitor can be enhanced when the operation of the low-boiling separation column is carried out in the presence of molecular oxygen.

A high-boiling substance containing an acrylic ester is withdrawn from the bottom of the rectifying column and supplied to a high-boiling separation column, and an acrylic ester component is recovered from the top of the high-boiling separation column. The high-boiling substance withdrawn from the bottom of the high-boiling separation column may be discharged as waste oil, or may be further introduced into a thin-film evaporator to recover an acrylic ester, after which it may be discharged as waste oil. On the other hand, an acrylic ester in the distillate from the high-boiling separation column and/or the thin-film evaporator is supplied to the low-boiling separation column for its recovery.

All or part of the distillate from the high-boiling separation column and/or the thin-film evaporator is mixed with water to extract and remove high-boiling acid components such as maleic acid and β-acryloxypropionic acid contained together with an acrylic ester in the distillate into a water phase, and the organic phase is supplied to the low-boiling separation column to recover the acrylic ester. At this time, the distillate from the high-boiling separation column may be supplied without any treatment to the low-boiling separation column, and all or part of the distillate from the thin-film evaporator may be mixed with water to carry out an extraction treatment. In this way, the extraction treatment of high-boiling acid components can reduce the amount of waste oil without increasing the amount of acid components contained in the product acrylic ester. Further, it can expand the accepted range of raw material acrylic acid. In this case, low-purity acrylic acid containing relatively great amounts of high-boiling acid components, for example, even acrylic acid containing from 10 to 5,000 ppm of maleic acid and/or from 10 to 5,000 ppm of β-acryloxypropionic acid, can be used as a raw material, and as shown in the following Examples, acrylic acid containing from 10 to 500 ppm of maleic acid and from 10 to 3,600 ppm of β-acryloxypropionic acid can preferably be used as a raw material.

Incidentally, as water to be mixed with all or part of the distillate, a process wastewater generated in a step of producing an acrylic ester may preferably be used. Examples of the process wastewater may include reaction water generated in the esterification reaction and steam drain exhausted in the case of using a steam ejector to reduce pressure in a pressure reduction step included in a step of producing an acrylic ester. In this way, the cost for wastewater treatment is not increased because of no increase in the amount of wastewater by making use of wastewater discharged from a step of producing an acrylic ester without introducing fresh water from outside the system.

Further, the ratio of water to be used to extract and remove the high-boiling acid components relative to the distillate from the high-boiling separation column and/or the thin-film evaporator may preferably be within a range of from 0.5 to 2.0, more preferably from 0.8 to 1.5, by mass ratio.

The production process of the present invention will be described below in more detail by reference to FIGS. 1 and 2. The production process of the present invention comprises supplying a high-boiling substance containing an acrylic ester, which is withdrawn from the bottom of a rectifying column, to a high-boiling separation column and/or a thin-film evaporator to separate it into an acrylic ester component and a high-boiling substance, the separated acrylic ester component being taken out as a distillate and supplied to a low-boiling separation column for its recovery. At this time, all or part of the distillate from the high-boiling separation column and/or the thin-film evaporator is mixed with water to extract and remove high-boiling impurities in the distillate into a water phase, and the obtained organic phase is supplied to the low-boiling separation column for its recovery. Therefore, the production process of the present invention is not limited to the production processes shown in FIGS. 1 and 2, and can be carried out by adding appropriate modifications and/or changes to these production processes unless such modifications and/or changes depart from the purport of the present invention.

Figure 1:
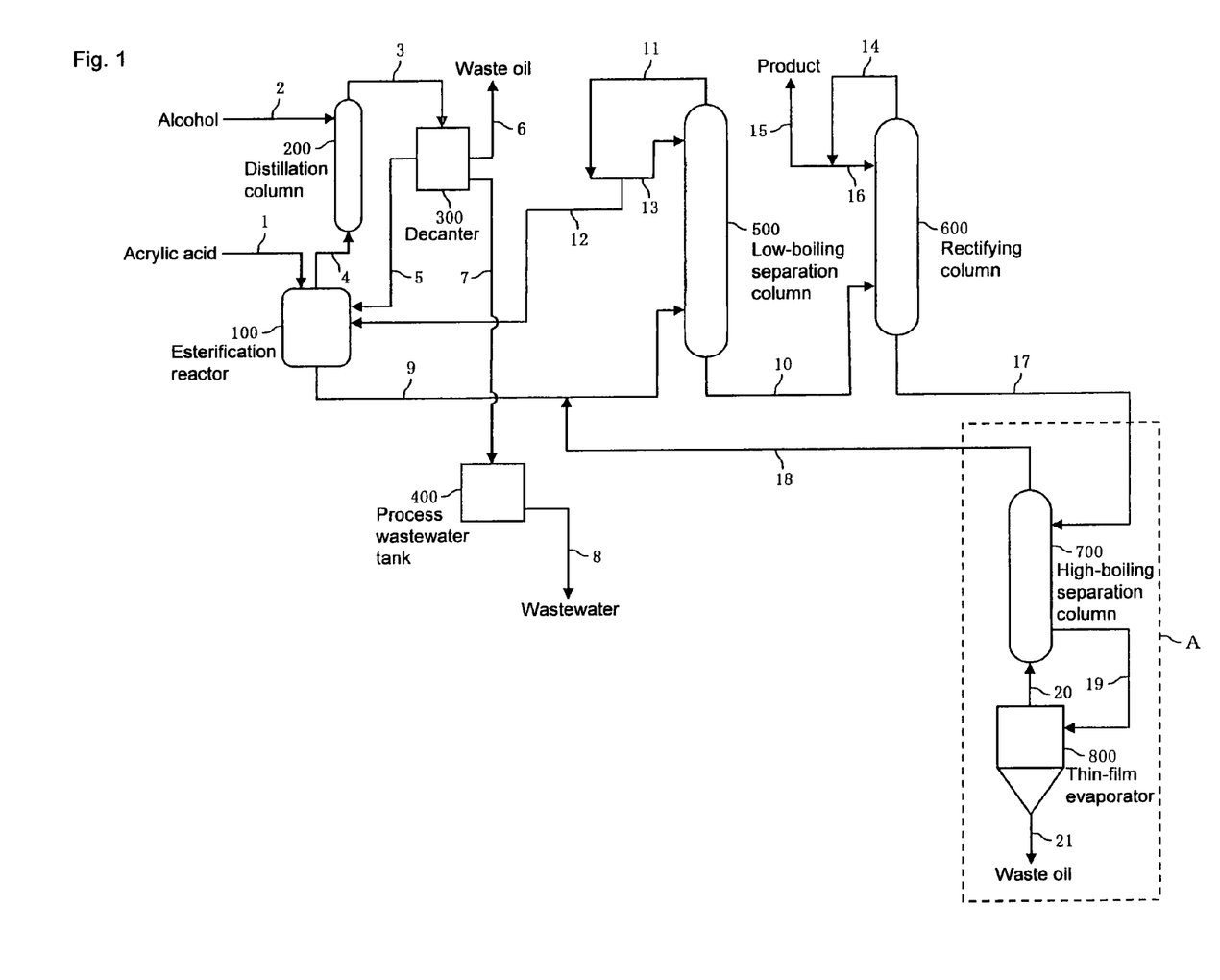
FIG. 1 is a schematic diagram showing one example of the production process, which is preferred for carrying out the production process of the present invention and is the production process used in Examples 1, 2, and 5.

FIG. 1 is a schematic diagram showing one example of the preferred production process to carry out the production process of the present invention. This production process is characterized in that high-boiling acid components are decreased from the bottom liquid of a rectifying column 600 using a high-boiling separation column 700 and a thin-film evaporator 800 in a portion designated as "A", and then all or part of the distillate containing an acrylic ester separated and recovered is circulated to a low-boiling separation column 500.

Acrylic acid is supplied through a line 1 to an esterification reactor 100 filled with a strongly acidic cation exchange resin. An alcohol is also supplied through a line 2 and a distillation column 200 to the reactor 100. An alcohol and reaction water are distilled out and introduced through a line 4 into the decanter 300. In the decanter 300, a water phase and an organic phase composed mainly of an alcohol are separated. Then, part of the organic phase is supplied through a line 5 to the esterification reactor 100, and the residue of the organic phase is sent through a line 6 as waste oil to a waste-oil treatment step. On the other hand, the water phase is stored through a line 7 in a process wastewater tank 400, and sent through a line 8 as wastewater to an alcohol recovery step or a wastewater treatment step.

An esterification product containing a generated ester, unreacted acrylic acid, an unreacted alcohol, and generated water is supplied through a line 9 from the reactor 100 to the low-boiling separation column 500 for its distillation. The bottom liquid of the low-boiling separation column 500 contains substantially all the amount of acrylic ester, and is supplied through a line 10 to the rectifying column 600. The top liquid of the low-boiling separation column 500 contains unreacted acrylic acid, an unreacted alcohol, and generated water, and discharged through a line 11 to separate into a water phase and an organic phase composed mainly of acrylic acid and an alcohol. Then, part of the organic phase is circulated as a circulated liquid through a line 12 to the esterification reactor 100, and the residue of the organic phase is circulated as reflux through a line 13 to the low-boiling separation column 500. On the other hand, the water phase is sent through a line not shown in the figure as wastewater to an alcohol recovery step or a wastewater treatment step.

The acrylic ester supplied to the rectifying column 600, after rectified, is discharged from the top of the rectifying column 600 through a line 14; part thereof becomes a finished product through a line 15, and the residual part is circulated as reflux through a line 16 to the rectifying column 600. The bottom liquid of the rectifying column is a high-boiling substance containing high-boiling acid components such as maleic acid and β-acryloxypropionic acid together with a small amount of acrylic ester, and is supplied through a line 17 to the high-boiling separation column 700.

The top liquid of the high-boiling separation column 700 (referred to as "distillate" in some cases) contains the acrylic ester separated and recovered, and all or part of the top liquid is circulated through a line 18 and the line 9 to the low-boiling separation column 500. The high-boiling substance containing high-boiling acid components such as maleic acid and β-acryloxypropionic acid is sent from the bottom of the thin-film evaporator 800 through a line 21 to a waste-oil treatment step.

In the production process shown in FIG. 1, the high-boiling separation column 700 and the thin-film evaporator 800 are used to separate and recover the acrylic ester contained in the bottom liquid of the rectifying column 600; however, it is not necessary to use both of them, and for example, it is possible that, using only the high-boiling separation column 700, the top liquid of the high-boiling separation column 700, containing the acrylic ester separated and recovered, is circulated to the low-boiling separation column 500, and the bottom liquid of the high-boiling separation column 700, containing high-boiling acid components such as maleic acid and β-acryloxypropionic acid, is sent as waste oil to a waste-oil treatment step; or using only the thin-film evaporator 800, a distillate containing the acrylic ester separated and recovered is withdrawn from the top of the thin-film evaporator 800 and circulated to the low-boiling separation column 500, and a residual liquid containing high-boiling acid components such as maleic acid and β-acryloxypropionic acid is discharged from the bottom of the thin-film evaporator 800 and sent as waste oil to a waste-oil treatment step.

In such a production of an acrylic ester, esterification reaction is carried out so that the conversion of acrylic acid is always kept constant, and therefore, the composition of an esterification product is stable and the operation conditions of the low-boiling separation column 500 are also kept stably. That is, the operation temperature of the low-boiling separation column 500 is constant, and the composition and amount of the organic phase to be circulated as a circulated liquid to the esterification reactor 100 are both constant.

Figure 2:
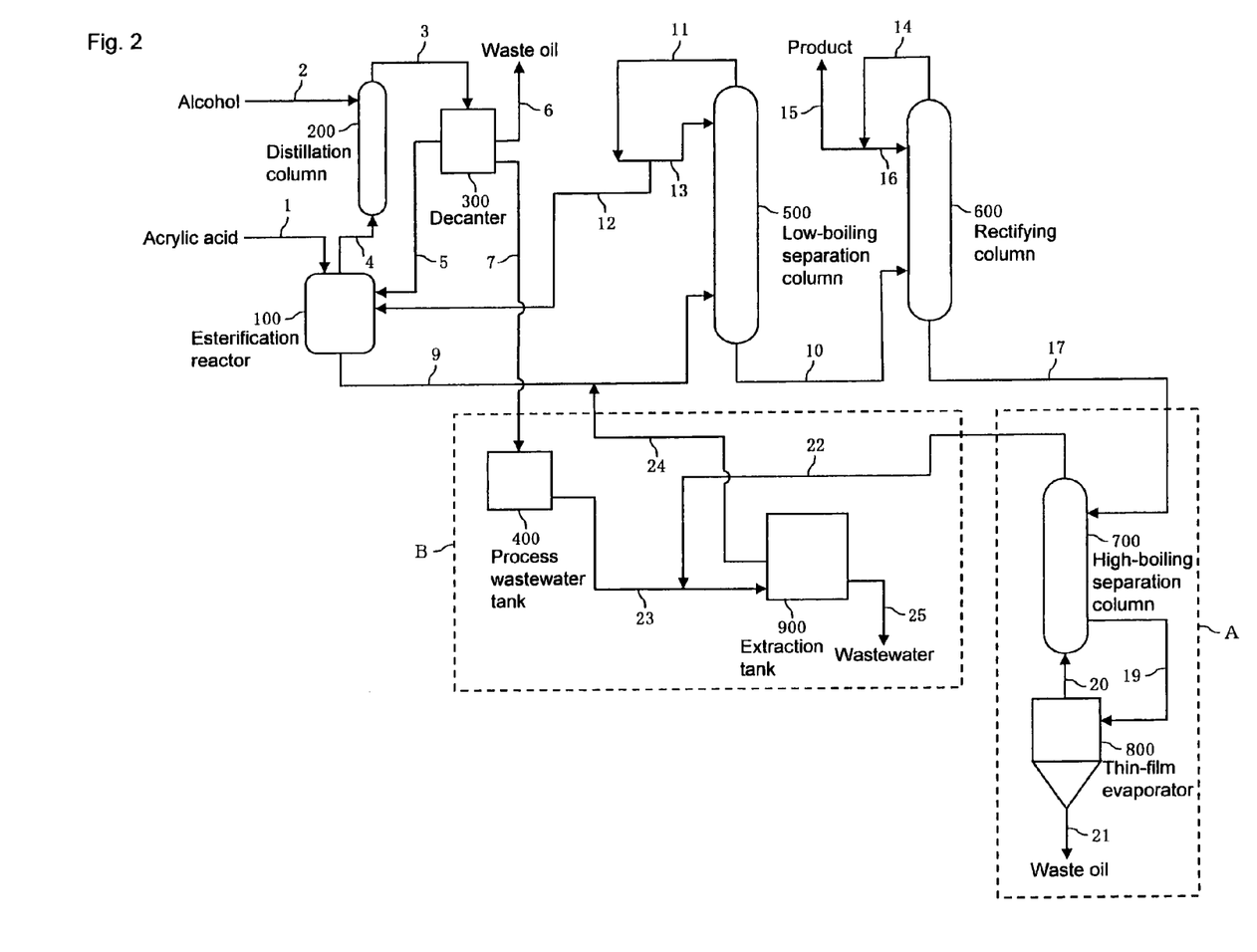
FIG. 2 is a schematic diagram showing another example of the production process, which is preferred for carrying out the production process of the present invention and is the production process used in Examples 3, 4, and 6.

FIG. 2 is a schematic diagram showing another example of the preferred production process to carry out the production process of the present invention. This production process is characterized in that a high-boiling acid substance containing an acrylic ester, which is withdrawn from the bottom of the rectifying column 600, is supplied to a high-boiling separation column 700 and a thin-film evaporator 800 in a portion designated as "A" to separate it into an acrylic ester component and a high-boiling substance, the separated acrylic ester component being taken out as a distillate, and all or part of the distillate is mixed with water in a portion designated as "B" to extract and remove high-boiling acid components in the distillate into a water phase, the obtained organic phase being supplied to the low-boiling separation column 500 for its recovery. Further, this production process is the same as the production process shown in FIG. 1 up to the stage of reducing high-boiling acid components from the bottom liquid of the rectifying column 600 using the high-boiling separation column 700 and the thin-film evaporator 800, that is, except for a portion designated as "B". Therefore, there will be described herein a step of extracting and removing high-boiling acid components contained in the top liquid of the high-boiling separation column 700 (referred to as "water extraction step" in some times) In FIG. 2, the same equipments as in FIG. 1 are designated by the same numbers.

All or part of the top liquid of the high-boiling separation column 700 is supplied through a line 22 and a line 23 to an extraction tank 900. At this time, it is supplied to the extraction tank 900 after being mixed in the line 23 with wastewater from the process wastewater tank 400. In the extraction tank 900, high-boiling acid components such as maleic acid and β-acryloxypropionic acid are extracted and removed into a water phase. Then, an organic phase containing an acrylic ester is circulated through the line 24 and the line 9 to the low-boiling separation column 500. On the other hand, the water phase containing high-boiling acid components such as maleic acid and β-acryloxypropionic acid is sent through a line 25 as wastewater to a wastewater treatment step. As water to be used to extract and remove high-boiling acid components, any water discharged in the production process may be used, although it is not particularly limited, and process water generated in the production process of an acrylic ester, including reaction water, may preferably be used.

In the production process shown in FIG. 2, the step of extracting, with water, all or part of the top liquid of the high-boiling separation column 700 is carried out in a portion designated as "B"; however, all or part of the top liquid of the high-boiling separation column 700 may be circulated without any treatment to the low-boiling separation column 500, and only for the distillate from the thin-film evaporator 800, the step of extracting, with water, all or part of the distillate may be carried out in a portion designated as "B".

In FIGS. 1 and 2, the mixing ratio of wastewater from the process wastewater tank 400 to be used to extract and remove high-boiling acid components, relative to the distillate from the high-boiling separation column 700 or the thin-film evaporator 800, i.e., the distillate containing an acrylic ester separated and recovered, may preferably be within a range of from 0.5 to 2.0, more preferably from 0.8 to 1.5, by mass ratio. When the mixing ratio is within this range, high-boiling acid components can efficiently be extracted and removed into a water phase, and an acrylic ester from which high-boiling acid components have sufficiently been removed can be circulated to the low-boiling separation column 500.

EXAMPLES

The present invention will be described below in more detail by way of Examples, but the present invention is not limited to the following Examples. The present invention can be put into practice after appropriate modifications or variations within a range meeting the gists described above and later, all of which are included in the technical scope of the present invention.

Example 1

To the esterification reactor 100 shown in FIG. 1 were supplied 400 kg/h of acrylic acid containing from 10 to 50 ppm of maleic acid and from 100 to 500 ppm of β-acryloxypropionic acid, 740 kg/h of 2-ethylhexanol, and 1,590 kg/h of a recovered alcohol liquid, and after 20 days of operation, the reaction was carried out at a reaction temperature of 85° C. and a conversion of acrylic acid of 50%, thereby giving a product acrylic ester at a yield of 990 kg/h from the top of the rectifying column 600. At this time, 25 kg/h of waste oil was discharged from the bottom of the thin-film evaporator 800, and 115 kg/h of the distillate from the high-boiling separation column 700 was circulated to the low-boiling separation column 500. The acid components contained in the obtained product acrylic ester were in an amount of from 25 to 35 ppm (in terms of acrylic acid). The measurement of acid components in the product acrylic ester was carried out by the titration of acid components (the same shall apply hereinafter). The results are shown in Table 1.

Example 2

To the esterification reactor 100 shown in FIG. 1 were supplied 400 kg/h of acrylic acid containing from 10 to 50 ppm of maleic acid and from 100 to 500 ppm of β-acryloxypropionic acid, 740 kg/h of 2-ethylhexanol, and 1,590 kg/h of a recovered alcohol liquid, and after 230 days of operation, the reaction was carried out at a reaction temperature of 100° C. and a conversion of acrylic acid of 50%, thereby giving a product acrylic ester at a yield of 965 kg/h from the top of the rectifying column 600. At this time, 50 kg/h of waste oil was discharged from the bottom of the thin-film evaporator 800, and 90 kg/h of the distillate from the high-boiling separation column 700 was circulated to the low-boiling separation column 500. The acid components contained in the obtained product acrylic ester were in an amount of from 25 to 35 ppm (in terms of acrylic acid). The results are shown in Table 1.

Example 3

To the esterification reactor 100 shown in FIG. 2 were supplied 400 kg/h of acrylic acid containing from 10 to 50 ppm of maleic acid and from 100 to 500 ppm of β-acryloxypropionic acid, 740 kg/h of 2-ethylhexanol, and 1,590 kg/h of a recovered alcohol liquid, and after 20 days of operation, the reaction was carried out at a reaction temperature of 85° C. and a conversion of acrylic acid of 50%, thereby giving a product acrylic ester at a yield of 1,000 kg/h from the top of the rectifying column 600. At this time, 15 kg/h of waste oil was discharged from the bottom of the thin-film evaporator 800, and 125 kg/h of the distillate from the high-boiling separation column 700 and 140 kg/h of wastewater from the wastewater tank 400 were mixed and supplied to the extraction tank 900 shown in FIG. 2. The water phase was removed as wastewater, and the organic phase containing an acrylic ester was circulated to the low-boiling separation column 500. The acid components contained in the obtained product acrylic ester were in an amount of from 25 to 35 ppm (in terms of acrylic acid). The results are shown in Table 1.

Example 4

To the esterification reactor 100 shown in FIG. 2 were supplied 400 kg/h of acrylic acid containing from 10 to 50 ppm of maleic acid and from 100 to 500 ppm of β-acryloxypropionic acid, 740 kg/h of 2-ethylhexanol, and 1,590 kg/h of a recovered alcohol liquid, and after 230 days of operation, the reaction was carried out at a reaction temperature of 100° C. and a conversion of acrylic acid of 50%, thereby giving a product acrylic ester at a yield of 997 kg/h from the top of the rectifying column 600. At this time, 18 kg/h of waste oil was discharged from the bottom of the thin-film evaporator 800, and 125 kg/h of the distillate from the high-boiling separation column 700 and 140 kg/h of wastewater from the wastewater tank 400 were mixed and supplied to the extraction tank 900 shown in FIG. 2. The water phase was removed as wastewater, and the organic phase containing an acrylic ester was circulated to the low-boiling separation column 500. The acid components contained in the obtained product acrylic ester were in an amount of from 25 to 35 ppm (in terms of acrylic acid). The results are shown in Table 1.

Comparative Example 1

Figure 3:
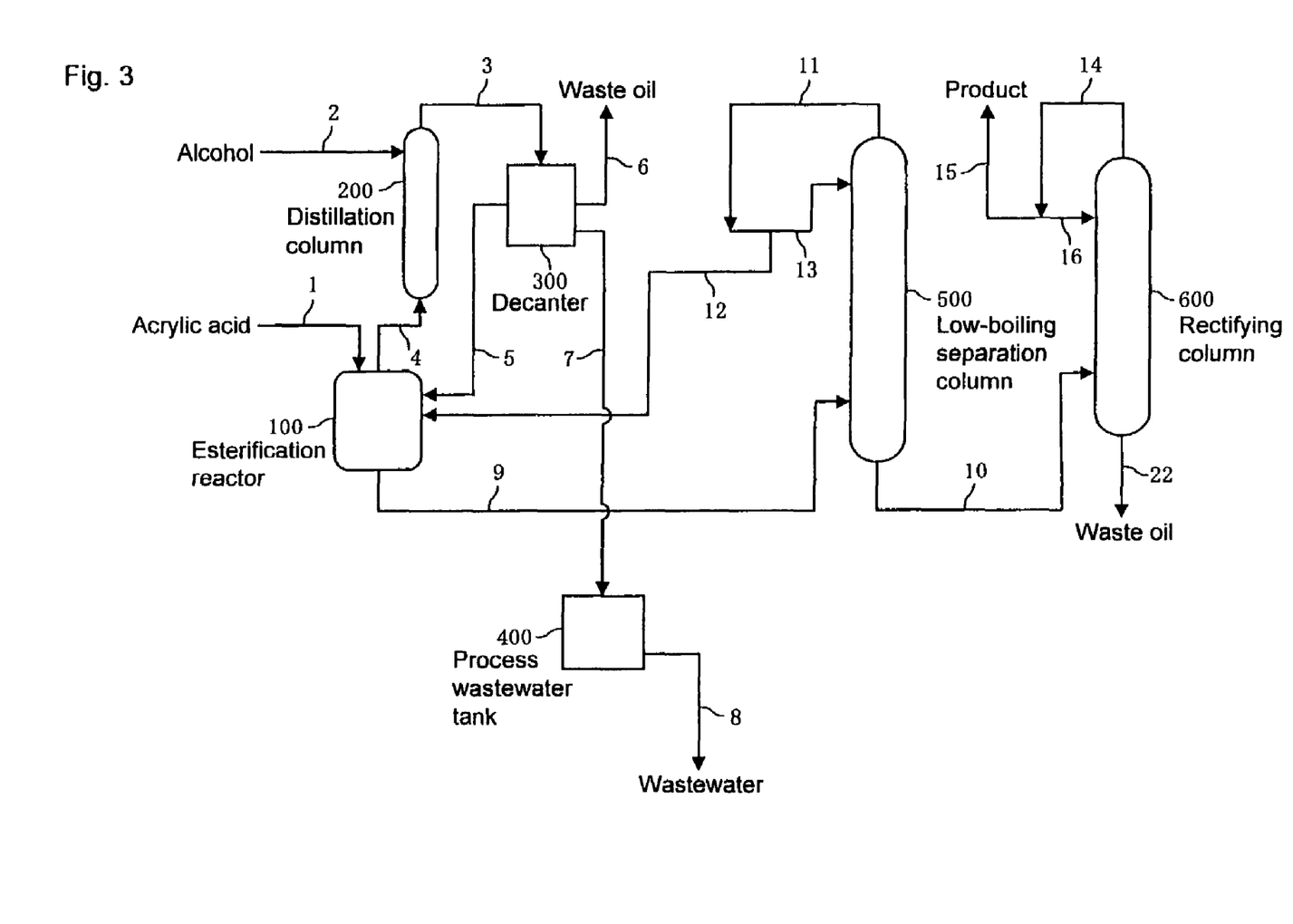
FIG. 3 is a schematic diagram showing the production process used in Comparative Examples 1, 2, and 3.

To the esterification reactor 100 shown in FIG. 3 were supplied 400 kg/h of acrylic acid containing from 10 to 50 ppm of maleic acid and from 100 to 500 ppm of β-acryloxypropionic acid, 740 kg/h of 2-ethylhexanol, and 1,590 kg/h of a recovered alcohol liquid, and after 20 days of operation, the reaction was carried out at a reaction temperature of 85° C. and a conversion of acrylic acid of 50%, thereby giving a product acrylic ester at a yield of 815 kg/h from the top of the rectifying column 600. At this time, 200 kg/h of waste oil was discharged from the bottom of the rectifying column 600. The acid components contained in the obtained product acrylic ester were in an amount of from 25 to 35 ppm (in terms of acrylic acid). The results are shown in Table 1.

Comparative Example 2

To the esterification reactor 100 shown in FIG. 3 were supplied 400 kg/h of acrylic acid containing from 10 to 50 ppm of maleic acid and from 100 to 500 ppm of β-acryloxypropionic acid, 740 kg/h of 2-ethylhexanol, and 1,590 kg/h of a recovered alcohol liquid, and after 230 days of operation, the reaction was carried out at a reaction temperature of 100° C. and a conversion of acrylic acid of 50%, thereby giving a product acrylic ester at a yield of 615 kg/h from the top of the rectifying column 600. At this time, 400 kg/h of waste oil was discharged from the bottom of the rectifying column 600. The acid components contained in the obtained product acrylic ester were in an amount of from 25 to 35 ppm (in terms of acrylic acid). The results are shown in Table 1.

Example 5

To the esterification reactor 100 shown in FIG. 1 were supplied 400 kg/h of acrylic acid containing from 100 to 500 ppm of maleic acid and from 500 to 3,600 ppm of β-acryloxypropionic acid, 740 kg/h of 2-ethylhexanol, and 1,590 kg/h of a recovered alcohol liquid, and after 230 days of operation, the reaction was carried out at a reaction temperature of 100° C. and a conversion of acrylic acid of 50%, thereby giving a product acrylic ester at a yield of 975 kg/h from the top of the rectifying column 600. At this time, 40 kg/h of waste oil was discharged from the bottom of the thin-film evaporator 800, and 90 kg/h of the distillate from the high-boiling separation column 700 was circulated to the low-boiling separation column 500. The acid components contained in the obtained product acrylic ester were in an amount of from 220 to 280 ppm (in terms of acrylic acid). The results are shown in Table 1.

Example 6

To the esterification reactor 100 shown in FIG. 2 were supplied 400 kg/h of acrylic acid containing from 100 to 500 pm of maleic acid and from 500 to 3,600 ppm of β-acryloxypropionic acid, 740 kg/h of 2-ethylhexanol, and 1,590 kg/h of a recovered alcohol liquid, and after 230 days of operation, the reaction was carried out at a reaction temperature of 100° C. and a conversion of acrylic acid of 50%, thereby giving a product acrylic ester at a yield of 997 kg/h from the top of the rectifying column 600. At this time, 18 kg/h of waste oil was discharged from the bottom of the thin-film evaporator 800, and 125 kg/h of the distillate from the high-boiling separation column 700 and 140 kg/h of wastewater from the process wastewater tank 400 were mixed and supplied to the extraction tank 900 shown in FIG. 2. The water phase was removed as wastewater, and the organic phase containing an acrylic ester was circulated to the low-boiling separation column 500. The acid components contained in the obtained product acrylic ester were in an amount of from 35 to 50 ppm (in terms of acrylic acid). The results are shown in Table 1.

Comparative Example 3

To the esterification reactor 100 shown in FIG. 3 were supplied 400 kg/h of acrylic acid containing from 100 to 500 ppm of maleic acid and from 500 to 3,600 ppm of β-acryloxypropionic acid, 740 kg/h of 2-ethylhexanol, and 1,590 kg/h of a recovered alcohol liquid, and after 230 days of operation, the reaction was carried out at a reaction temperature of 100° C. and a conversion of acrylic acid of 50%, thereby giving a product acrylic ester at a yield of 845 kg/h from the top of the rectifying column 600. At this time, 170 kg/h of waste oil was discharged from the bottom of the rectifying column 600. The acid components contained in the obtained product acrylic ester were in an amount of from 150 to 170 ppm (in terms of acrylic acid). The results are shown in Table 1.

TABLE 1

| | Number of figure showing production process | Amount of impurities contained in raw material acrylic acid (ppm) | | Yield of product acrylic ester (kg/h) | Amount of acid components contained in product acrylic ester (ppm) | Amount of waste oil (kg/h) |
| --- | --- | --- | --- | --- | --- | --- |
| | | Maleic acid | β-Acryloxy-propionic acid | | | |
| Example 1 | FIG. 1 | from 10 to 50 | from 100 to 500 | 990 | from 25 to 35 | 25 |
| Example 2 | FIG. 1 | from 10 to 50 | from 100 to 500 | 965 | from 25 to 35 | 50 |
| Example 3 | FIG. 2 | from 10 to 50 | from 100 to 500 | 1,000 | from 25 to 35 | 15 |
| Example 4 | FIG. 2 | from 10 to 50 | from 100 to 500 | 997 | from 25 to 35 | 18 |
| Comp. Ex. 1 | FIG. 3 | from 10 to 50 | from 100 to 500 | 815 | from 25 to 35 | 200 |
| Comp. Ex. 2 | FIG. 3 | from 10 to 50 | from 100 to 500 | 615 | from 25 to 35 | 400 |
| Example 5 | FIG. 1 | from 100 to 500 | from 500 to 3,600 | 975 | from 220 to 280 | 40 |
| Example 6 | FIG. 2 | from 100 to 500 | from 500 to 3,600 | 997 | from 35 to 50 | 18 |
| Comp. Ex. 3 | FIG. 3 | from 100 to 500 | from 500 to 3,600 | 845 | from 150 to 170 | 170 |

As can be seen from Table 1, in Examples 1 and 2, the yield of a product acrylic ester was able to be kept high in such a manner that when an acrylic ester was produced using the production process shown in FIG. 1, a high-boiling substance containing an acrylic ester, which was withdrawn from the bottom of a rectifying column, was supplied to a high-boiling separation column and/or a thin-film evaporator to separate it into an acrylic ester component and a high-boiling substance, and the separated acrylic ester component was taken out as a distillate and supplied to a low-boiling separation column for its recovery, thereby decreasing the loss of an acrylic ester from waste oil. At this time, no problem was caused on the quality of a product.

Further, in Examples 3 and 4, when an acrylic ester was produced using the production process shown in FIG. 2, a high-boiling substance containing an acrylic ester, which was withdrawn from the bottom of a rectifying column, was supplied to a high-boiling separation column and/or a thin-film evaporator to separate it into an acrylic ester component and a high-boiling product, and the separated acrylic ester component was taken out as a distillate, all or part of which was mixed with water to extract and remove high-boiling acid components such as maleic acid and β-acryloxypropionic acid contained together with an acrylic ester in the distillate into a water phase, the water phase being discharged as wastewater, and the organic phase being supplied to a low-boiling separation column to recover an acrylic ester. In Examples 3 and 4 including a step of water extraction, it became possible to further decrease the loss of an acrylic ester from waste oil and improve the yield of a product acrylic ester, compared with those of Examples 1 and 2, without deteriorating the quality of a product. In the production of an acrylic ester controlling the constant conversion of acrylic acid, the reaction temperature is raised with extending the duration of using a strongly acidic cation exchange resin accordingly, in which case the amount of high-boiling acid components such as β-acryloxypropionic acid influencing the quality of a product increases, and therefore, it becomes necessary to make a response by increasing the amount of waste oil to maintain the quality of a product acrylic ester. However, according to the conditions of Example 4 into which a step of water extraction was introduced, the stable quality of a product acrylic ester and the stable yield of a product were able to be obtained without remarkably increasing the amount of waste oil from the early period of reaction in Example 3. The yield of a product under conditions of a high reaction temperature was quite noticeable as compared with Example 2 and Comparative Example 2.

In contrast, in Comparative Examples 1 and 2, when an acrylic ester was produced using the production process shown in FIG. 3, the bottom liquid of a rectifying column was subjected as waste oil without any treatment to a step of waste treatment, and therefore, although the amount of high-boiling acid components contained in the product acrylic ester obtained as part of the top liquid of the rectifying column did not change as compared with Examples 1 to 4, the yield of a product acrylic ester was remarkably decreased as compared with Examples 1 to 4, and the amount of waste oil was remarkably increased as compared with Examples 1 to 4.

From these facts, it can be understood that the loss of an acrylic ester from waste oil can be decreased and the yield of a product acrylic ester can be increased, without deteriorating the quality of a product acrylic ester, by supplying the bottom liquid of a rectifying column to a high-boiling separation column and/or a thin-film evaporator, separating and taking out, as a distillate, an acrylic ester remaining in the bottom liquid of the rectifying column from a high-boiling substance, and supplying the distillate to a low-boiling separation column for its recovery; and further, that a decrease in the loss of an acrylic ester from waste oil can more stably be achieved to improve production efficiency, by introducing a step of water extraction in which all or part of the distillate from the high-boiling separation column and/or the thin-film evaporator is mixed with water generated in the production process to extract and remove high-boiling acid components into a water phase, which is discharged as wastewater, and a organic phase is supplied to the low-boiling separation column to recover an acrylic ester.

Further, in Example 5, an acrylic ester was produced in almost the same manner as described in Examples 1 and 2 using the production process shown in FIG. 1, except that a low-purity acrylic acid was used as a raw material. Although the amount of high-boiling acid components contained in the product acrylic ester was great, in spite of using a low-purity acrylic acid as a raw material, the yield of a product acrylic ester and the amount of waste oil were at about the same level as those in Examples 1 and 2.

Further, in Example 6, an acrylic ester was produced in almost the same manner as described in Examples 3 and 4 using the production process shown in FIG. 2, except that a low-purity acrylic acid was used as a raw material. In spite of using a low-purity acrylic acid as a raw material, the yield of a product acrylic ester was increased as compared with Example 5, and the amount of waste oil was remarkably decreased as compared with Example 5, both of which were by no means inferior to Examples 3 and 4 using a relatively high-purity acrylic acid as a raw material.

In contrast, in Comparative Example 3, an acrylic ester was produced in almost the same manner as described in Comparative Examples 1 and 2 using the production process shown in FIG. 3, except that a low-purity acrylic acid was used as a raw material. The yield of a product acrylic ester was remarkably decreased as compared with Examples 5 and 6, and although the amount of high-boiling acid components contained in the product acrylic ester was smaller than that in Example 5, it was very great as compared with Example 6, and the amount of waste oil was remarkably increased as compared with Examples 5 and 6.

From these facts, it can be understood that the loss of an acrylic ester form waste oil can be suppressed on a low level, without deteriorating the quality of a product acrylic ester, to improve production efficiency and achieve the stable production, even when low-purity acrylic acid containing great amounts of high boiling acid components such as maleic acid and β-acryloxypropionic acid is used as a raw material, or even when relatively high-purity acrylic acid is used as a raw material, by introducing a step of water extraction in which the bottom liquid of a rectifying column is supplied to a high-boiling separation column and/or a thin-film evaporator, an acrylic ester remaining in the bottom liquid of the rectifying column is taken out as a distillate through separating a high-boiling substance, all or part of the distillate is mixed with water generated in the production process to extract and remove high-boiling acid components into a water phase, which is discharged as wastewater, and an organic phase is supplied to a low-boiling separation column to recover an acrylic ester.

As described above, the production process of the present invention makes it possible to stably achieve a large reduction in the production cost of an acrylic ester.

The present invention provides a process for producing an acrylic ester using acrylic acid containing high-boiling acid components, such as maleic acid and β-acryloxypropionic acid, influencing the loss in quality of an acrylic ester and the unit consumption of raw materials, and an aliphatic or alicyclic alcohol having from 5 to 8 carbon atoms, as raw materials, and a strongly acidic cation exchange resin as a catalyst, which process is excellent from an economical point of view because it can eliminate the conventional problems to maintain the stable quality and the low unit consumption of raw materials, and which process makes a great contribution to the filed of acrylic ester production.

The invention claimed is:

1. A process for producing an acrylic ester by supplying acrylic acid and an aliphatic or alicyclic alcohol having from 5 to 8 carbon atoms to an esterification reactor to cause an esterification reaction using a strongly acidic cation exchange resin as a catalyst in the reactor, the process comprising supplying an obtained reaction product to a low-boiling separation column to distill an alcohol, acrylic acid, and water from the top of the low-boiling separation column, and separating them into a water phase and an organic phase containing the alcohol and acrylic acid, the organic phase being circulated as a circulated liquid to the reactor, supplying a crude acrylic ester, which is withdrawn from the bottom of the low-boiling separation column, to a rectifying column, taking out a rectified acrylic ester from the top of the rectifying column, and supplying a high-boiling substance containing an acrylic ester, which is withdrawn from the bottom of the rectifying column, to a high-boiling separation column and/or a thin-film evaporator to separate it into an acrylic ester component and a high-boiling substance, the separated acrylic ester component being taken out as a distillate, mixing all or part of the distillate with water to extract and remove a high-boiling acid component contained in the distillate into a water phase, and supplying an obtained organic phase to the low-boiling separation column for its recovery.

2. The process according to claim 1, wherein water to be used to extract and remove the high-boiling acid component is a process wastewater generated in a step of producing an acrylic ester.

3. The process according to claim 1, wherein a ratio of water to be used to extract and remove the high-boiling acid component, relative to the distillate taken from the high-boiling separation column and/or the thin-film evaporator, is within a range of from 0.5:1 to 2.0:1 by mass ratio.

4. The process according to claim 1, wherein acrylic acid to be used as a raw material in the process for producing an acrylic ester comprises from 10 to 5,000 ppm of maleic acid and/or from 10 to 5,000 ppm of $\beta$-acryloxypropionic acid.

5. The process according to claim 2, wherein a ratio of water to be used to extract and remove the high-boiling acid component, relative to the distillate taken from the high-boiling separation column and/or the thin-film evaporator, is within a range of from 0.5:1 to 2.0:1 by mass ratio.

6. The process according to claim 2, wherein acrylic acid to be used as a raw material in the process for producing an acrylic ester comprises from 10 to 5,000 ppm of maleic acid and/or from 10 to 5,000 ppm of $\beta$-acryloxypropionic acid.

7. The process according to claim 5, wherein acrylic acid to be used as a raw material in the process for producing an acrylic ester comprises from 10 to 5,000 ppm of maleic acid and/or from 10 to 5,000 ppm of $\beta$-acryloxypropionic acid.

8. The process according to claim 5, wherein acrylic acid to be used as a raw material in the process for producing an acrylic ester comprises from 10 to 5,000 ppm of maleic acid and/or from 10 to 5,000 ppm of $\beta$-acryloxypropionic acid.

* * * * *